United States Patent [19]

Cooper et al.

[11] 4,234,491
[45] Nov. 18, 1980

[54] STEROID SYNTHESIS PROCESS USING MIXED ANHYDRIDE

[75] Inventors: Gary F. Cooper, Menlo Park; Albert R. Van Horn, Los Altos, both of Calif.

[73] Assignee: Syntex (U.S.A.) Inc., Palo Alto, Calif.

[21] Appl. No.: 22,667

[22] Filed: Mar. 22, 1979

Related U.S. Application Data

[62] Division of Ser. No. 916,443, Jun. 19, 1978, Pat. No. 4,158,012.

[51] Int. Cl.$^3$ .................................. C07D 317/12
[52] U.S. Cl. .................. 260/340.9 AS; 260/397.3; 260/545 R
[58] Field of Search .................. 260/340.9 AS

[56] References Cited

U.S. PATENT DOCUMENTS

| | | | |
|---|---|---|---|
| 3,413,314 | 11/1968 | Amiard et al. | 260/340.9 AS |
| 4,024,166 | 5/1977 | Sauer et al. | 260/397.3 |

FOREIGN PATENT DOCUMENTS

| | | |
|---|---|---|
| 1042633 | 9/1966 | United Kingdom. |
| 1096769 | 12/1967 | United Kingdom. |
| 1141856 | 2/1969 | United Kingdom. |

*Primary Examiner*—Ethel G. Love
*Attorney, Agent, or Firm*—Alan M. Krubiner; Gerard A. Blaufarb

[57] ABSTRACT

The tricyclic intermediate

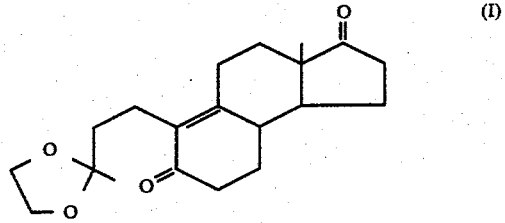

is prepared in a three step sequence from the bicyclic intermediate

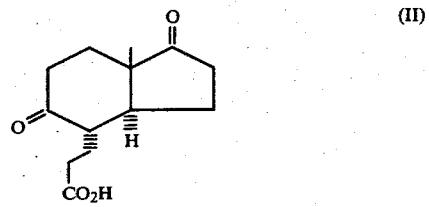

The key step of this process involves the addition of a Grignard reagent to a mixed anhydride. Tricyclic compound of formula (I) may be readily converted by known methods to valuable steroids.

8 Claims, No Drawings

STEROID SYNTHESIS PROCESS USING MIXED ANHYDRIDE

This is a division of application Ser. No. 916,443, filed June 19, 1978, now U.S. Pat. No. 4,158,012.

BACKGROUND OF THE INVENTION

A large number of valuable steroids drugs have substituents in the 17α position which are introduced by addition to a 17-ketone. A particularly important steroid of this type is 17α-ethynyl-19-nortestosterone (NET), a valuable progestational agent. The precursor 17-ketosteroid, 19-norandrost-4-en-3,17-dione (NAD) has been prepared by a variety of methods. In general, synthesis of this compound from bicyclic or tricyclic intermediates involves working with compounds wherein the eventual 17-keto group is protected, usually in a reduced oxidation state, for example, as an ester or ether of the 17β-alcohol.

It would be valuable to have a synthetic method available that would afford a 17-ketosteroid wherein it was not necessary to utilize intermediates having a protected 17-ketone, but rather wherein such keto intermediates themselves could be utilized.

DESCRIPTION OF THE INVENTION

The present invention relates to a novel process for the preparation of the tricyclic compound of the formula

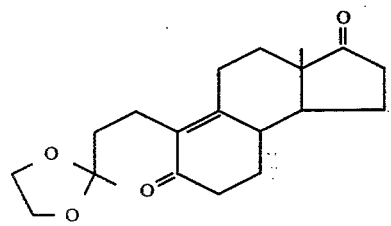

from the bicyclic compound

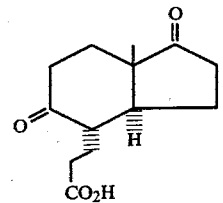

More particularly the present invention relates to a three step process for such conversion, namely: (a) conversion of the compound of formula (II) to its mixed anhydride with trimethylacetic acid (pivalic acid), (b) addition of a Grignard reagent to this mixed anhydride, and (c) cyclization to the tricyclic compound of formula (I). In particular, the key step of Grignard addition to the mixed anhydride results in extremely high yields of the desired addition product and, surprisingly, is unexpectedly superior when compared with the identical reaction utilizating mixed anhydrides formed with other acids.

The present process is illustrated in more detail in the following reaction scheme.

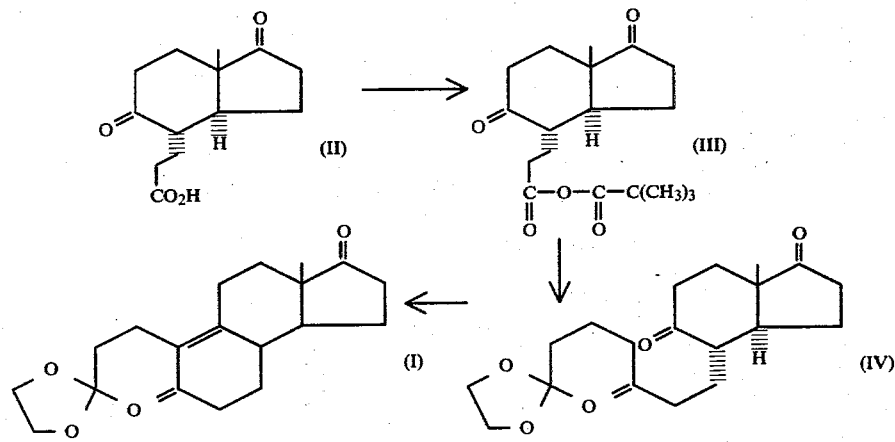

In the first step, the known bicyclic diketopropionic acid of formula (II) is converted to its pivalic acid mixed anhydride. This mixed anhydride is represented by formula (III). This reaction is effected by treating the starting acid of formula (II) with trimethylacetyl chloride (pivaloyl chloride) in the presence of a tertiary amine, preferably a trialkylamine, most preferably triethylamine. While the proportions of the reagents may vary to a certain extent it is preferred that the compound of formula (II), the pivaloyl chloride and the amine be utilized in approximately equimolar amounts. The reaction is preferably carried out in an inert organic solvent, for example, an ether such as diethyl ether or tetrahydrofuran. Tetrahydrofuran is especially preferred. The use of an ether in this reaction step and the avoidance of substantial excesses of acid chloride and amine reagents allows the subsequent Grignard addition step to be carried out in the same solvent system without need to purify the mixed anhydride or to remove the tertiary amine hydrochloride formed.

The mixed anhydride formation step is carried out at a temperature between about −50° and +20° C., most preferably between about −30° and −10° C., for a period of time about 15 minutes to 2 hours, most preferably between about 15 minutes and 45 minutes. In a preferred embodiment, triethylamine is utilized as the amine and the progress of the anhydride formation reaction is followed by precipitation of triethylamine hydrochloride from the reaction mixture.

The mixed anhydride may be isolated by filtration and evaporation of the solvent; however, it is generally preferred not to isolate this intermediate but to utilize the tetrahydrofuran solution of mixed anhydride directly for the next reaction step.

In the next reaction step, the mixed anhydride of formula (III) is treated with a Grignard reagent

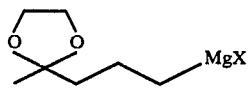

wherein X is chloro or bromo, i.e., a Grignard reagent prepared from 5-chloro-2-pentanone ethylene ketal or 5-bromo-2-pentanone ethylene ketal, preferably the former. While the proportions of the Grignard reagent and the mixed anhydride are not narrowly critical, to obtain the high degree of regioselectivity desired it is preferred to utilize approximately equimolar amounts of these reagents. The Grignard reagent is prepared in the standard manner from the corresponding haloketal according to the method of C. P. Forbes et al, *J. C. S. Perkins I*, 2353 (1977). The Grignard reagent is preferably employed as a solution in tetrahydrofuran, at a concentration of approximately 0.5 to 2.0 M, preferably about 1.0 M. It is generally preferred that the Grignard reagent be added to the solution of the mixed anhydride, at a temperature between about $-80°$ and $-55°$ C., most preferably between about $-70°$ and 65° C. and, after addition is complete, the reaction is continued for a period of time of between about 30 minutes and 2 hours, preferably about 1 hour, and then the reaction mixture is allowed to warm up to between about $-30°$ and $-10°$ C. before being quenched with water.

Workup of the reaction mixture in the usual manner affords the triketoketal of formula (IV).

In the final step, the compound of formula (IV) is cyclized in the presence of base to the tricyclic compound of formula (I). The basic cyclization is preferably effected by means of an alkali metal hydroxide such as sodium hydroxide or potassium hydroxide, in an aqueous solvent medium, most preferably an aqueous alcoholic solvent medium such as aqueous methanol. While the quantity of alkali relative to compound of formula (IV) is not narrowly critical it is generally preferred that an excess of base be utilized, most preferably a 2 to 10 fold molar excess. The cyclization reaction is carried out at a temperature between about 40° and 80° C., most preferably at the reflux temperature of the aqueous alcholic medium, and for a period of time of between about 15 minutes and 2 hours, most preferably about 1 hour. Preferably the cyclization reaction is carried out under an inert atmosphere such as nitrogen. The reaction mixture is worked up in the usual manner involving neutralization and removal of the organic solvent followed by extraction of the organic products into an appropriate organic solvent. The reaction product is generally of a purity sufficient for further conversion, for example to, NAD. If desired, however, purified compound of formula (I) may be obtained by chromatography, for example, utilizing silica gel. Compound (I) is a known compound; see, for example, German Offen. No. 1,903,565, Oct. 23, 1969.

It has been found that by using the above three-step procedure, without isolating or purifying intermediates, an approximately 80% yield of tricyclic compound of formula (I), based upon starting diketo acid of formula (II), is obtained. Even more advantageous is the avoidance of the need to protect or otherwise modify the eventual 17-ketone during this synthetic scheme.

A variety of other mixed anhydrides of the acid of formula (II) have been prepared and subjected to the above described Grignard addition and cyclization process. However, it was found that the use of the specific mixed anhydride of the present invention, namely, the mixed anhydride with pivalic acid, provides unexpectedly superior results. It is particularly surprising that during the critical step of Grignard addition to the mixed anhydride, the Grignard reagent exhibits a high degree of regioselectivity and adds to the carbonyl group of the diketopropionic acid portion of the mixed anhydride to a much greater degree than to the pivaloyl carbonyl group or either of the two keto groups on the bicyclic nucleus, thus resulting in high yields of the desired product (I) after cyclization, in the order of 80%, from starting (II). It is also surprising that other mixed anhydrides, including those of substantially hindered acids such as 2,4,6-trimethylbenzoic acid, do not provide comparable yields of tricyclic compound of formula (I).

As mentioned above, the tricyclic compound of formula (I) may be readily converted to known useful steroid compounds such as NAD. Thus, the compound of formula (I) may be selectively hydrogenated, for example, utilizing a palladium on carbon catalyst in methanol in the presence of triethylamine, followed by acid cyclization, for example, cyclization with aqueous hydrochloric acid, preferably in the presence of an alcohol solvent such as methanol, to afford NAD.

The following examples further illustrate the process of the present invention. In the examples all compounds are of the natural stereochemical configuration. However, the present process is equally applicable to the optical antipodes thereof as well as mixtures of the above, for example, racemic mixtures.

EXAMPLE 1

A solution of 5.00 g (+)—7aα-methyl-2,3,3aα,4,5,6,-7,7a-octahydro-1H-inden-1,5-dione-4α-(3-propionic acid), m.p. 108°–109° C., 48 ml dry tetrahydrofuran (THF) and 2.12 g. triethylamine was cooled under nitrogen to $-30°$ C. After stirring 5 minutes at $-30°$ 2.56 g trimethylacetylchloride (99%) was injected by syringe. A white precipitate began to form immediately. The mixture was allowed to warm to $-20°$ C. ($+3°$) and stirred at this temperature for 30 min. An aliquot was filtered and evaporated to dryness. The resulting (+)-7aβ-methyl2,3,3aα,4,5,6,7,7a-octahydro-1H-inden-1,5-dione-4β-(3-propionic acid) pivalic acid mixed anhydride exhibited the following characteristic IR peaks (neat): 1820, 1745, 1710, 1010 and 1040 cm$^{-1}$.

The reaction mixture was cooled to $-70°$ C. and 22.1 ml 0.95 M Grignard reagent in tetrahydrofuran (prepared from 5-chloro-2-pentanone ethylene ketal) was added over 40 minutes keeping the temperature between $-67°$ and $-70°$ C. After stirring for 1 additional hour the mixture was allowed to warm to $-20°$ C. and was treated with 25 ml water. After vigorous stirring for 5 minutes the tetrahydrofuran was stripped off while minimizing contact of the solution with air. An aliquot was worked up to afford (+) 3a,7a-trans-4-[7,7-(ethylendioxy)-3-oxo-octyl]-7aβ-methyl-perhydroindan-1,5-dione (Formula IV):

IR: 1740, 1710, 1370 cm$^{-1}$
MS: m/e=350,335
NMR: α=3.94 (s, 4H), 1.30 (s, 3H), 1.16 (s, 3H) ppm.

The remaining product was treated with 30 ml methanol followed by 7.1 g KOH dissolved in 20 ml water which was washed in with an additional 30 ml methanol. The resulting slurry was refluxed under nitrogen for 1 hour, cooled to room temperature, and neutralized by the addition of 6.75 ml glacial acetic acid. The methanol was stripped off under vacuum and the resulting heterogeneous mixture was extracted once with 40 ml diethyl ether and three times with 25 ml diethyl ether portions. The combined organic extracts were washed with 20 ml concentrated aqueous $Na_2CO_3$, 20 ml water and 20 ml brine and dried over $Na_2SO_4$.

Filtration and concentration in vacuo afforded (+)-3,3-ethylenedioxy-4,5-seco-19-norandrost-9-en-5,17-dione (formula I) as a colorless oil:

IR: 1740, 1665, 1605, 1055 cm$^{-1}$
UV: λ max.=248 nm (ε=13,100, MeOH)
$[\alpha]_D^{25}$= +43.1° (Lit+44.5°±2°)
MS: m/e=331, 317
NMR: δ=3.91 (s, 4H), 1.34 (s, 3H), 1.02 (s, 3H) ppm.

EXAMPLE 2

Comparison of Mixed Anhydrides

A solution of 5.00 g diketo acid of formula II (20.98 mmole), 48 ml dry THF, and 2.12 g triethylamine (20.98 mmole) was cooled to −30° C. and treated with one equivalent (20.98 mmole) of the appropriate acid halide. The precipitation of triethylamine hydrochloride was evidence that the formation of the mixed anhydride was occurring. If no precipitate formed the temperature was raised until it did so. When the reaction was complete, as determined by IR spectroscopy of an aliquot, the mixture was cooled to −70° C. One equivalent (20.98 mmole) of the Grignard reagent in THF (approximately 1 Molar), as in Example 1, was added dropwise over 40 minutes keeping the temperature between −67° and −70° C. The Grignard reagent was washed in with 2 ml dry THF and the resulting mixture was stirred for 1 hour at −70° C. The temperature was raised to −20° C. and 25 ml water was added. After 5 minutes of stirring the THF was removed in vacuo. The flask was set up for reflux under nitrogen and 60 ml methanol and 7.1 g KOH dissolved in 20 ml water was added. The mixture was refluxed for 1 hour under nitrogen, cooled to room temperature and neutralized with 6.75 ml glacial acetic acid. The methanol was stripped off and the organic products were extracted with diethyl ether or methylene chloride. The extracts were washed with concentrated aqueous $Na_2CO_3$ and brine and dried over $Na_2SO_4$. Crude product was isolated by filtration and concentration in vacuo. Pure compound of formula (I) was isolated by preparative thin layer chromatography on silica gel using 60/40 ethyl acetate/hexane or by column chromatography on silica gel using an ethyl acetate/hexane gradient.

The results were as follows with X being the mixed anhydride moiety.

| X = | Temperature During Grignard Step | Yield of I |
| --- | --- | --- |
| isobutyloxycarbonyloxy | −70° | 22.9 |
| diethylphosphonyloxy | −70° | 38.2 |
| p-toluenesulfonyloxy | −70° | 6.6 |
| pivaloyloxy | −70° | 80 |
| 2-chlorobenzoyloxy | −70° | 49 |
| 2,6-dichlorobenzoyloxy | −70° | 50 |
| 2,4,6-trimethylbenzoyloxy | −70° | 60 |

The above clearly demonstrates the unexpectedly superior results obtained with the pivalic acid mixed anydride.

EXAMPLE 3

8.1 g (+)-3,3-Ethylenedioxy-4,5-seco-19-norandrost-9-en-5,17-dione, 1.51 g. of 5% palladium on carbon and 12.7 ml triethylamine in 131 ml methanol was stirred under atmospheric pressure of hydrogen at 25° C. until uptake ceased. The reaction mixture was filtered and the filtrate diluted with 16 ml methanol and 11.6 ml of 12 N hydrochloric acid and then heated at reflux for 3 hours under nitrogen. About 75 ml of solvent was then distilled off, the mixture cooled and neutralized with sufficient 33% w/w aqueous NaOH to bring to pH 7 and 275 ml water was added. After stirring at room temprature overnight the mixture was filtered and the filtrate washed with water and dried. The crude product was treated with refluxing hexane for one hour, cooled, filtered and dried to afford 5.26 g (+)-19-norandrost-4-en-3,17-dione (NAD), m.p. 166°-171° C.

What is claimed is:

1. A process for the preparation of the compound represented by the formula

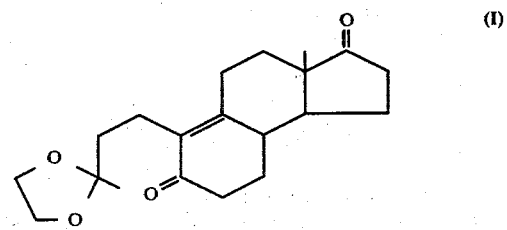

which comprises
(a) treating a compound represented by the formula

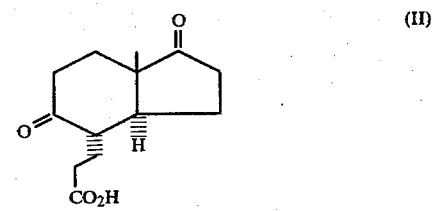

with pivaloyl chloride in the presence of a tertiary amine to afford a mixed anhydride represented by the formula

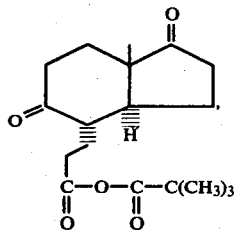
(III)

(b) treating said mixed anhydride with a Grignard reagent of the formula

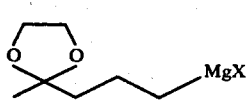

wherein X is chloro or bromo, in an ether solvent at a temperature between −55° and −80° C., followed by treatment with water, to afford a triketoketal compound represented by the formula

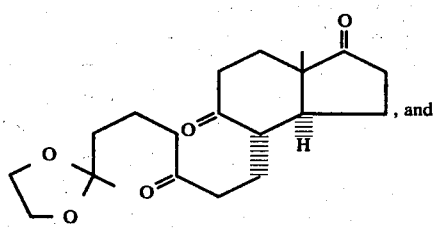
(IV)
, and (c) treating said triketoketal compound with base in an aqueous medium at a temperature between about 50° and 80° C. to afford said compound of formula (I).

2. The process of claim 1 wherein, in step (a), said tertiary amine is triethylamine.

3. The process of claim 1 wherein, in step (b), said Grignard reagent is

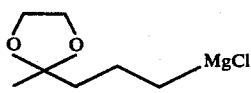

and said ether solvent is tetrahydrofuran.

4. The process of claim 1 wherein, in step (b), said temperature is between about −65° and +70° C.

5. The process of claim 1 wherein, in step (c), said base is an alkali metal hydroxide, said aqueous medium is aqueous methanol and said temperature is the reflux temperature of said medium.

6. A process for the preparation of the compound represented by the formula

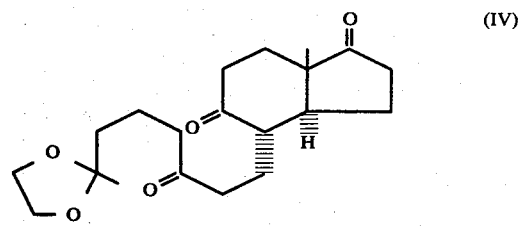
(IV)

which comprises treating a mixed anhydride of the formula

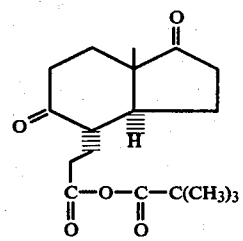
(III)

with a Grignard reagent of the formula

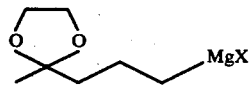

wherein X is chloro or bromo, in an ether solvent at a temperature between about −55° and −80° C., followed by treatment with water.

7. The process of claim 6 wherein said Grignard reagent is

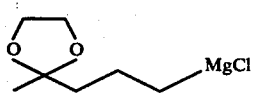

and said solvent is tetrahydrofuran.

8. The process of claim 6 wherein said temperature is between about −65° and −70° C.

* * * * *